US012765803B2

(12) United States Patent
Greenberg et al.

(10) Patent No.: US 12,765,803 B2
(45) Date of Patent: Oct. 20, 2026

(54) SYSTEMS AND/OR METHODS FOR ASSESSING NEUROMUSCULAR BLOCK STATUS WITHOUT STIMULATION

(71) Applicant: BLOCKsynop, Inc., Highland, MD (US)

(72) Inventors: Robert S. Greenberg, Baltimore, MD (US); Wayne I. Sternberger, Highland, MD (US)

(73) Assignee: BLOCKsynop, Inc., Highland, MD (US)

( * ) Notice: Subject to any disclaimer, the term of this patent is extended or adjusted under 35 U.S.C. 154(b) by 0 days.

(21) Appl. No.: 19/367,497

(22) Filed: Oct. 23, 2025

(65) Prior Publication Data

US 2026/0047777 A1 Feb. 19, 2026

Related U.S. Application Data

(63) Continuation of application No. PCT/US2024/053856, filed on Oct. 31, 2024.

(Continued)

(51) Int. Cl.

| | |
|---|---|
| ***A61B 5/11*** | (2006.01) |
| ***A61B 5/00*** | (2006.01) |
| ***A61B 5/389*** | (2021.01) |

(52) U.S. Cl.

CPC ............ *A61B 5/1106* (2013.01); *A61B 5/389* (2021.01); *A61B 5/742* (2013.01)

(58) Field of Classification Search

CPC ........ A61B 5/1106; A61B 5/389; A61B 5/742

See application file for complete search history.

(56) References Cited

U.S. PATENT DOCUMENTS 4,595,018 A * 6/1986 Rantala ................ A61B 5/7217 600/554

5,195,531 A * 3/1993 Bennett ............... A61M 16/104 600/587

(Continued)

FOREIGN PATENT DOCUMENTS

| | | |
|---|---|---|
| CA | 2748730 | 7/2010 |
| CA | 2913074 | 12/2014 |

(Continued)

OTHER PUBLICATIONS

Motamed, "Intraoperative Monitoring of Neuromuscular Blockade" Monitoring of Neuromuscular; Blockade. Life 2023, 13, 1184, https://doi.org/10.3390life13051184, pp. 1-13.

(Continued)

*Primary Examiner* — May A Abouelela
*Assistant Examiner* — Yasmeen S Warsi
(74) *Attorney, Agent, or Firm* — Nixon & Vanderhye PC

(57) ABSTRACT

Neuromuscular block characterization techniques are disclosed. A muscle movement measurement device generates, unprompted by impulse stimulation to a subject from an external source, at least one signal representative of muscle movement measurements at at least one location of a body of the subject while the subject is experiencing neuromuscular paralysis caused by biophysiological processes at neuromuscular synapses throughout the body including remote from the at least one location. A processing circuit runs a neuromuscular block analysis module that receives the at least one signal, analyzes the muscle movement measurements embedded in the at least one signal, and determines a degree of neuromuscular blockade associated with the neuromuscular paralysis being experienced by the subject. The processing circuitry further generates, for dis- (Continued)

play via a display device, an indication of the degree of the neuromuscular blockade at each said location on the body.

17 Claims, 8 Drawing Sheets

Related U.S. Application Data

(60) Provisional application No. 63/547,027, filed on Nov. 2, 2023.

(56) References Cited

U.S. PATENT DOCUMENTS

| | | | |
|---|---|---|---|
| 5,372,140 | A | 12/1994 | Pomfrett |
| 5,906,208 | A | 5/1999 | Ishikawa et al. |
| 5,964,713 | A | 10/1999 | Nomura et al. |
| 6,002,960 | A | 12/1999 | Sternberger et al. |
| 7,848,797 | B2 | 12/2010 | Kong et al. |
| 8,439,836 | B2 | 5/2013 | Storm |
| 8,463,370 | B2 | 6/2013 | Korhonen et al. |
| 8,506,502 | B2 | 8/2013 | Gilhuly |
| 9,888,869 | B2 | 2/2018 | Sternberger et al. |
| 11,179,066 | B2 | 11/2021 | Kaifosh et al. |
| 11,324,430 | B2 | 5/2022 | Sternberger |
| 2003/0007504 | A1 | 1/2003 | Berry et al. |
| 2007/0276609 | A1* | 11/2007 | Greenwald ............ A61B 5/374 607/46 |
| 2008/0071386 | A1 | 3/2008 | Mcbean et al. |
| 2010/0081963 | A1 | 4/2010 | Gilhuly |
| 2013/0204156 | A1* | 8/2013 | Hampton ............. A61B 5/4052 600/546 |
| 2014/0012157 | A1 | 1/2014 | Gilhuly |
| 2014/0148796 | A1 | 5/2014 | Gharib et al. |
| 2014/0235991 | A1 | 8/2014 | Gadsby |
| 2015/0141773 | A1 | 5/2015 | Einav et al. |
| 2015/0283365 | A1 | 10/2015 | Dacey et al. |
| 2016/0157753 | A1 | 6/2016 | Sternberger |
| 2016/0228030 | A1 | 8/2016 | Fadem |
| 2016/0324446 | A1 | 11/2016 | Prerau et al. |
| 2017/0360334 | A1 | 12/2017 | Oksala et al. |
| 2019/0134391 | A1 | 5/2019 | Druke et al. |
| 2019/0175078 | A1 | 6/2019 | Chen |
| 2019/0216354 | A1 | 7/2019 | Sternberger |
| 2020/0093401 | A1 | 3/2020 | Blink |
| 2021/0060337 | A1 | 3/2021 | Wybo et al. |
| 2021/0145358 | A1 | 5/2021 | Bray, Jr. |
| 2021/0178157 | A1 | 6/2021 | Druke et al. |

FOREIGN PATENT DOCUMENTS

| | | |
|---|---|---|
| CA | 3055961 | 9/2018 |
| CA | 3144957 | 12/2020 |
| CN | 103886215 | 6/2014 |
| CN | 107560066 | 1/2018 |
| CN | 113729644 | 12/2021 |
| EP | 2438850 | 4/2012 |
| JP | 2002-186591 | 7/2002 |
| JP | 2009-061179 | 3/2009 |
| KR | 10-2012-0091875 | 8/2012 |
| WO | 2012/115346 | 8/2012 |
| WO | 2016/134273 | 8/2016 |
| WO | 2018/141850 | 8/2018 |

OTHER PUBLICATIONS

Jan. 8, 2025 International Search Report and Written Opinion issued in International Patent Application No. PCT/US2024/053856, pp. 1-66.

Lopez et al. ".Neuromuscular monitoring and its importance in neuromuscular blockade." (2012). Retrieved on Dec. 28, 2024 (Dec. 28, 2024) from <https://www.sciencedirect.com/science/article/pii/S2256208712000028> entire document.

Motamed. "Intraoperative monitoring of neuromuscular blockade." Life 13.5 (2023):1184. May 15, 2023 (May 15, 2023) Retrieved on Dec. 28, 2024 (Dec. 28, 2024) from https://pme.ncbi.nlm.nih.gov/articles/PMC10223480/pdf/life-13-01184.pdf entire document.

Murphy et al. "Monitoring neuromuscular blockade." International anesthesiologyclinics 42.2 (2004): 25-40. Retrieved on Dec. 28, 2024 (Dec. 28, 2024) from https://faculty.washington.edu/ramaiahr/Review% 20Articles/Neuromuscular%20Monitoring.pdf entire document.

Yough et al., "Surface Electromyography Provides Neuromuscular Insights for Skill Acquisition in Microgravity" HHS Public Access Author manuscript Proc Int Astronaut Congr. Author manuscript; available in PMC 2023 May 2, pp. 1-17.

Kim et al., "Comparison of the effect of electromyogram activity during emergemence on anesthetic depth monitoring between phase lag entropy and bispectral index: a prospective observational study" Ann Palliat Med 2022;11(4):1290-1296 I https://dx/doi.org/10.21037/apm-21-847 pp. 1-7.

Schuller et al., "Response of the Conox quantitative electroencephalographic monitor to neuromuscular block in awake volunteers" Neuroscience and Neuroanaesthesia; British Journal of Anaesthesia, 135 (3): 660e667 (2025).

Hernandez et al., "Comparison of adductor pollicis and flexor hallucis brevis muscle electromyographic responses: a prospective cohort study" Reports of Original Investigations, https://doi.org/10.1007/s12630-025-03029-8 pp. 1-7.

Tan et al., "Innovations in Perioperative Medicine: Technologies to Improve Outcomes" Review Article, Int Anesthesiol Clin vol. 63, No. 3, Summer 2025, pp. 1-7.

Ebert et al., "Improving quantitative neuromuscular monitoring: an education initiative on stimulating electrode placement" Journal of Clinical Monitoring and Computing, Oct. 21, 2024, pp. 1-6.

Wedemeyer et al., "Accuracy and Precision of Three Accelermyographs, Three Electromyographs, and a Mechanomyograph Measuring the Train-of-four Ratio in the Absence of Neuromuscular Blocking Drugs" Anesthesiology vol. 141, No. 2, Perioperative Medicine, Aug. 2024, pp. 1-10.

Chinn et al., "Innovative Technology, Persistent Risk: Electrical Injury from an Automated Quantitative Neuromuscular Blockade Monitoring (QNMT) Device" Rapid Response to questions from readers, APSF Newsletter Oct. 2023, 3 pages.

Rodney et al., "Neuromuscular block management: evidence-based principles and practice" BJA Education, 24(1): 13e22 (2024) pp. 1-10.

Renew et al., "Comparison of visual and electromyographic assessments with train-of-four stimulation of the ulnar nerve: a prospective cohort study" Reports of Original Investigations, Mar. 29, 2023, pp. 1-8.

Elise Hyman, "How to Implement the ASA Practice Guidelines for Neuromuscular Blockade" Twitch News, Mar. 13, 2023, 4 pages.

Multiple Contributors, "How to Pick a Quantitative Monitor for Neuromuscular Blockade" Twitch News, Jan. 19, 2023, 6 pages.

Murola et al., "Feasibility of electromyography (sEMG) in measuring muscular activity during spinal anaesthesia in patients undergoing knee arthroplasty" Acta Anaesthesiol Scand 2005; 49: pp. 558-562.

Thilen et al., "2023 American Society of Anesthesiologists Practice Guidelines for Monitoring and Antagonism of Neuromuscular Blockade: A Report by the American Society of Anesthesiologists Task Force on Neuromuscular Blockade" Practice Parameter, Anesthesiology 2023; vol. 138, No. 1, pp. 13-41.

May 15, 2026 International Preliminary Report in Patentability issued in International Application No. PCT/US2024/053856, pp. 1-18.

* cited by examiner

SYSTEMS AND/OR METHODS FOR ASSESSING NEUROMUSCULAR BLOCK STATUS WITHOUT STIMULATION

CROSS REFERENCE TO RELATED APPLICATIONS

This application is a continuation of International Application No. PCT/US2024/053856 filed on Oct. 31, 2024, which claims the benefit of U.S. Provisional Application No. 63/547,027 filed on Nov. 2, 2023, the entire contents of each of which are hereby incorporated herein by reference.

TECHNICAL FIELD

Certain example embodiments relate to techniques for objective monitoring of the effects of depolarizing and non-depolarizing neuromuscular blocking agents during the conduct, for example, of clinical management of a patient for surgery or intensive care.

BACKGROUND AND SUMMARY

Neuromuscular blockade, which also may be thought of as a form of neuromuscular paralysis, is frequently used in a variety of clinical contexts. For example, neuromuscular blockade is used to facilitate endotracheal intubation, improve or optimize surgical conditions (e.g., when used as part of an anesthetic for surgery), assist with artificial (e.g., mechanical) ventilation in patients (e.g., in an intensive care unit), etc. The administration of a neuromuscular blocking agent (NMBA) helps initiate and maintain neuromuscular blockade, e.g., by reducing or eliminating muscle tone. Current NMBAs are depolarizing (as in the case of, for example, succinylcholine) or non-depolarizing (as in the case of, for example, rocuronium, vecuronium, etc.). Both types of NMBA can result in effective paresis (muscle weakening) and paralysis.

Current depolarizing NMBAs are advantageous in some contexts. For example, succinylcholine is widely used as a depolarizing NMBA because of its rapid onset and short duration of action (e.g., when properly administered, paralysis usually takes place approximately 1 minute after administration and lasts approximately 7-12 minutes). Depolarizing agents effectively "over-stimulate" the muscular end-plate, thereby eliminating the opportunity for ongoing stimulation, leading to relaxation. That is, depolarizing agents flood the neuromuscular junction with acetylcholine-like chemicals to stimulate and sustain receptor agonism causing relaxation of the muscle contraction.

Current non-depolarizing NMBAs have chemical structures that are either steroidal or have a benzylisoquinolinium structure. Non-depolarizing agents, in general, interfere with the nerve end-plate released acetylcholine to encounter the receptor on the motor endplate, resulting in reduced or no activation of the muscular contraction. That is, non-depolarizing agents interfere with the natural stimulation of the receptor and inhibit activation of muscular contraction.

Clinicians (e.g., anesthesiologists, anesthetists, intensive care physicians, nurses, etc.) and/or others will want to assess the effectiveness of the agents and monitor the blockade when procedures such as those identified above are taking place. Assessment of neuromuscular blockade reveals the status of the neuromuscular junction, an example of which is shown schematically in FIG. 1. More particularly, the assessment of neuromuscular blockade, whether by a depolarizing or non-depolarizing agent, is geared towards revealing the degree to which the interface between the neural end-plate and the muscular unit has been interrupted leading to weakness.

Typically, clinicians and/or others rely on subjective feedback elicited from a patient to determine the effectiveness or state of a neuromuscular blockade. Current practice requires the administration of an electrical stimulation of a relevant nerve and concurrent observation of the resultant apparent muscular activity in the region of the myotome serviced by that nerve. More recently, advances in the observation of muscle response from stimulation include objective measurement of the coincident stimulation/muscle movement.

In essence, methods to assess the degree of neuromuscular inhibition (and muscle relaxation) invoke an electrical stimulation to elicit a "twitch." Various techniques using such stimulation can inform the clinician as to the degree of neuromuscular blockade. From a clinical perspective, under current practices, the effects of muscle relaxants typically are measured by characterizing the impact on repeated electrical nerve stimulation (e.g., low-moderate amplitude 2 Hz shock for 2 seconds, as in "train-of-four" or "TOF" monitoring) and comparing the amplitude of the resultant muscle movement for each stimulation. The decay in signals representing the decay in response of neuromuscular activation, and thus changes in the responsive "twitch" (e.g., from the first signal, either through or versus, the fourth signal) represents muscular contractions and informs on the degree of blockade. See, for example, Stephan R. Thilen et al., "2023 American Society of Anesthesiologists Practice Guidelines for Monitoring and Antagonism of Neuromuscular Blockade: A Report by the American Society of Anesthesiologists Task Force on Neuromuscular Blockade," Anesthesiology, vol. 138, no. 1, (January 2023): 13-41, which discusses TOF-related techniques that involve stimulation from an external source.

Conventional TOF monitoring involves placement of stimulating/shocking pads in strategic locations (e.g., over the ulnar nerve as it passes across the ulnar groove at the elbow or along the ulnar side of the arm) and sensors (e.g., muscle accelerometers or high amplitude electromyography elements) at the "target" muscle serviced by the stimulated nerve (e.g., the adductor pollicis muscle of the thumb). Repeated shocks/stimulations permit assessment over time, informing the clinician of the relative percent blockade afforded and the need (or lack of need) to re-dose the agent, to provide an "antidote" or reversal agent (e.g., neostigmine or sugammadex), or the effectiveness of said reversal agent, etc.

FIG. 2 shows classical examples of changes to TOF measurements, which may take place in some instances. It will be appreciated that FIG. 2 provides examples of the kind of data that TOF monitoring can show, and the specific FIG. 2 data will not be clinically present in all instances. In FIG. 2, the top TOF measurements show increasing weakness following administration of rocuronium. That is, comparing the first and fourth responses of a train-of-four with a non-depolarizing agent in this example reveals a substantial reduction in ratio (as the fourth response is significantly less than the first response), indicating a significant—and ultimately complete—blockade of the neuromuscular junction. The middle of FIG. 2 shows tetanic stimulation, which can be used in connection with TOF monitoring to help detect block at the neuromuscular junction in some instances. This approach is used to "prime" the neuromuscular junction by providing a "super-stimulation," which is then subjected to TOF stimulation. It can in some instances help to elicit a recognizable response when blockade is near maximal. The bottom of FIG. 2 shows TOF monitoring before and after sugammadex (an example reversal agent) has been administered, and it can be seen that the response is a prompt and sustained return to baseline (pre-block) condition following administration.

Unfortunately, there are a number of drawbacks with the current approaches. For example, these techniques require proper placement of stimulation electrodes, proper placement of the sensing electrode(s) (e.g., if not simply subjectively feeling the movement), and precisely administered electrical shocks for each assessment. An error in one or more of these areas may lead to inappropriate muscular responses and/or inappropriate interpretations of the responses. For example, improper placement of stimulation electrodes may lead to direct muscular stimulation and contraction rather than nerve stimulation and subsequent direct muscular stimulation and contraction/movement (thereby potentially (and inappropriately) indicating the effect of synapse propagation of signal rather than direct muscular stimulation of contraction). Finally, systems that use non-standard or variable stimulation regimens (e.g., power/amplitude, frequency, square-wave or sine-wave, and pulse frequency [e.g., 50 or 100 Hz] typical of tetanic stimulation) may have different effects at different synapse interspace block percentage and over time.

Certain example embodiments help address the above-described and/or other concerns. For example, certain example embodiments provide an approach for determining a neuromuscular block effect without the use of electro-stimulation/shock.

Certain example embodiments relate to techniques for neuromuscular blockade determination that include, for example, processing circuitry configured to passively receive muscle movement measurements, continuously analyze the muscle movement measurements (e.g., in, for example, a frequency domain) over time, and determine an effectiveness of a neuromuscular blocking agent based on the analysis of the muscle movement measurements. The techniques of certain example embodiments involve passive measures in that they do not require external stimulation from an electrical or non-electrical source. Advantageously, the assessment of neuromuscular blockade enabled by certain example embodiments may be continuous rather than aperiodic or even periodic.

One aspect of certain example embodiments relates to the use of advanced analysis of otherwise clinically imperceptible muscle movements, thereby obviating the need for electrical stimulation at a discrete site, and advantageously permitting the objective assessment of the degree of blockade (e.g., induced paralysis) at the neuromuscular junction. In this sense, the otherwise clinically imperceptible muscle movements that are detectable by certain example embodiments include those muscle movements that are undetectable by typical TOF analysis and other techniques that require a stimulated "twitch" to be "seen" or felt. As will be appreciated by those skilled in the art, certain example embodiments provide improvements because they obviate the need to subjectively assess, or "feel," a particular body part (e.g., a thumb) move. The kind of objective assessment provided by certain example embodiments can be particularly advantageous for both movements that are too small to be detected using conventional approaches and for measuring blockade close to the maximal amount. As will be appreciated from the description herein, certain example embodiments provide technical advantages in terms of providing potentially continuous measurements over a large dynamic range.

Another aspect of certain example embodiments relates to recognition of underlying "native" muscular contractions as a result of baseline ongoing natural stimulation at the neuromuscular junction, that is, without electrical stimulation, which advantageously affords a more continuous assessment of the degree to which the neuromuscular junction is affected. It is noted that ongoing and continuous measurement of the power changes in the frequency domain over time advantageously affords continuous measurement of the changes due to re-dosing or natural elimination of the effect of the NMBA in certain example instances.

As will be appreciated from the discussion that follows, the techniques disclosed herein can be used in connection with neuromuscular blockade assessment brought on by means other than administration of an NMBA. For example, mechanical means can cause motor blockade, e.g., as is common when a leg "falls asleep" from nerve compression, when there is a loss of motor strength from more central nerve impingement (e.g., from an extruded disk), etc. In some clinical instances, mechanical blockages may be induced. The techniques disclosed herein can be useful in assessing neuromuscular effect (and especially blockade) in those instances as well. For example, when a mechanical blockage is induced, a temporary spike may occur before a drop in an EMG signal. Certain example embodiments may recognize a temporary change (e.g., a preceding temporary increase in signal) and inform not only on the degree of neuromuscular blockade induced but also the type of blockade (e.g., to distinguish a chemically induced block from another type of block).

Although certain example embodiments involve sensor application at discrete sites related to motor nerve distribution, certain example embodiments alternatively or additionally may involve sensor application at a location different from (and potentially unrelated to) a specific nerve (e.g., at a different muscle mass).

In certain example embodiments, a neuromuscular block characterization system is provided. A muscle movement measurement device is configured to generate, unprompted by impulse stimulation to a subject from an external source, at least one signal representative of muscle movement measurements at at least one location of a body of the subject while the subject is experiencing neuromuscular paralysis caused by biophysiological processes at neuromuscular synapses throughout the body including remote from the at least one location. A processing circuit is configured to run a neuromuscular block analysis module, the module being configured to receive the at least one signal, analyze the muscle movement measurements embedded in the at least one signal, and determine a degree of neuromuscular blockade associated with the neuromuscular paralysis being experienced by the subject. The processing circuitry is further configured to generate, for display via a display device, an indication of the degree of the neuromuscular blockade at each said location on the body.

In certain example embodiments, a system comprises a transducer configured to generate a signal indicative of muscle movements of a body part unprompted by stimulation from an external source. The system is configured to generate an indication of neuromuscular blockade based on the signal generated by the transducer, the indication reflecting a degree of neuromuscular blockade affecting the body part.

In certain example embodiments, a method of characterizing neuromuscular block is provided. The method comprises generating, unprompted by impulse stimulation to a subject from an external source, at least one signal representative of muscle movement measurements at at least one location of a body of the subject while the subject is experiencing neuromuscular paralysis caused by biophysiological processes at neuromuscular synapses throughout the body including remote from the at least one location; analyzing the muscle movement measurements embedded in the at least one signal; determining a degree of neuromuscular blockade associated with the neuromuscular paralysis being experienced by the subject; and generating, for display via a display device, an indication of the degree of the neuromuscular blockade at each said location on the body.

In certain example embodiments, there is provided a non-transitory computer readable storage medium tangibly storing a program that, when executed, causes a processor to perform operations comprising: analyzing muscle movement measurements embedded in at least one received signal, the at least one received signal having been unprompted by impulse stimulation to a subject from an external source, the at least one received signal being representative of muscle movement measurements at at least one location of a body of the subject while the subject is experiencing neuromuscular paralysis caused by biophysiological processes at neuromuscular synapses throughout the body including remote from the at least one location; determining a degree of neuromuscular blockade associated with the neuromuscular paralysis being experienced by the subject; and generating, for display via a display device, an indication of the degree of the neuromuscular blockade at each said location on the body.

It will be appreciated that one or more separate devices can be responsible for gathering data, analyzing the gathered data, generating human-understandable output from the analyzed data, and/or actually outputting that information. For example, the neuromuscular block characterization system of certain example embodiments may encompass one or more devices. For instance, in embodiments where the neuromuscular block characterization system encompasses a plurality of devices, a first device may be or comprise a measurement device, and a second device may be or comprise a separate analysis and/or display device. Similarly, in certain example embodiments, a processing circuit may include one device that performs data gathering and/or analysis, and another that generates a display (e.g., for an integrated and/or external display device). In certain example embodiments, multiple measurement devices may provide data to an analysis and/or display device, a single measurement device may provide data to multiple analysis and/or display devices, etc.

It will be appreciated that certain example embodiments analyze electromyography signals to inform on neuromuscular blockade, including neuromuscular blockade caused by the administration of NMBAs. It should be made clear that changes seen in electromyography from the administration of NMBAs (e.g., reduction in signal power at specific frequencies) are to be distinguished from those seen from the administration of, for example, local anesthetics in the vicinity of a motor nerve. In the former, the effect is established at the neuromuscular endplate/synapse via the bloodstream—usually from an intravenous administration of the NMBA, although it can be the result of, for example, intramuscular administration and subsequent absorption into the bloodstream. This administration impacts the space between the nerve endplate and muscle leading to reduction or elimination of the [acetylcholine] signal and resultant paralysis of the muscle throughout the body by chemical means. The blockade of the motor endplate has no effect on afferent conduction (e.g., sensation) or the perception of pain.

In the case of neural blockade, however, with the administration of local anesthetics to a specific nerve, the reduction or elimination of the signal is created by the effect on the sodium channel from within the nerve cell, which stops the propagation of signal along the nerve to the endplate (that is, not at the endplate synapse itself). The administration of the local anesthetic must be performed in the region of the specific relevant nerve fibers (for example, the spinal canal [spinal, epidural], nerve plexus [e.g., lumbar plexus], or even the nerve itself [e.g., femoral nerve]) and the effect is limited to the muscle fibers innervated by the nerves related to the location of the local anesthetic administration. That is, muscles innervated by nerves not exposed to the local anesthetics will continue to propagate signal to muscles and display unaffected electromyograms. In the case of neural blockade assessment via EMG signal analysis, one application leverages the collocation of sensory fibers with muscle motor fibers to recognize a surrogate (motor blockade) for analgesia (sensory) blockade.

Thus, an EMG signal can show changes in both neuromuscular blockade and neural blockade. However, the actual changes are brought about by different biophysiological mechanisms and have different local (neural blockade) or general systemic (neuromuscular blockade) effects. As one skilled in the art will appreciate, these different mechanisms and different effects are not readily anticipated or clinically related, e.g., as neural blockade functions as a surrogate indicator of changes in sensation whereas neuromuscular blockade functions as an indicator of muscle paralysis.

The features, aspects, advantages, and example embodiments described herein may be used separately and/or applied in various combinations to achieve yet further embodiments of this invention.

BRIEF DESCRIPTION OF THE DRAWINGS

These and other features and advantages may be better and more completely understood by reference to the following detailed description of exemplary illustrative embodiments in conjunction with the drawings, of which.

DETAILED DESCRIPTION

Figure 1:
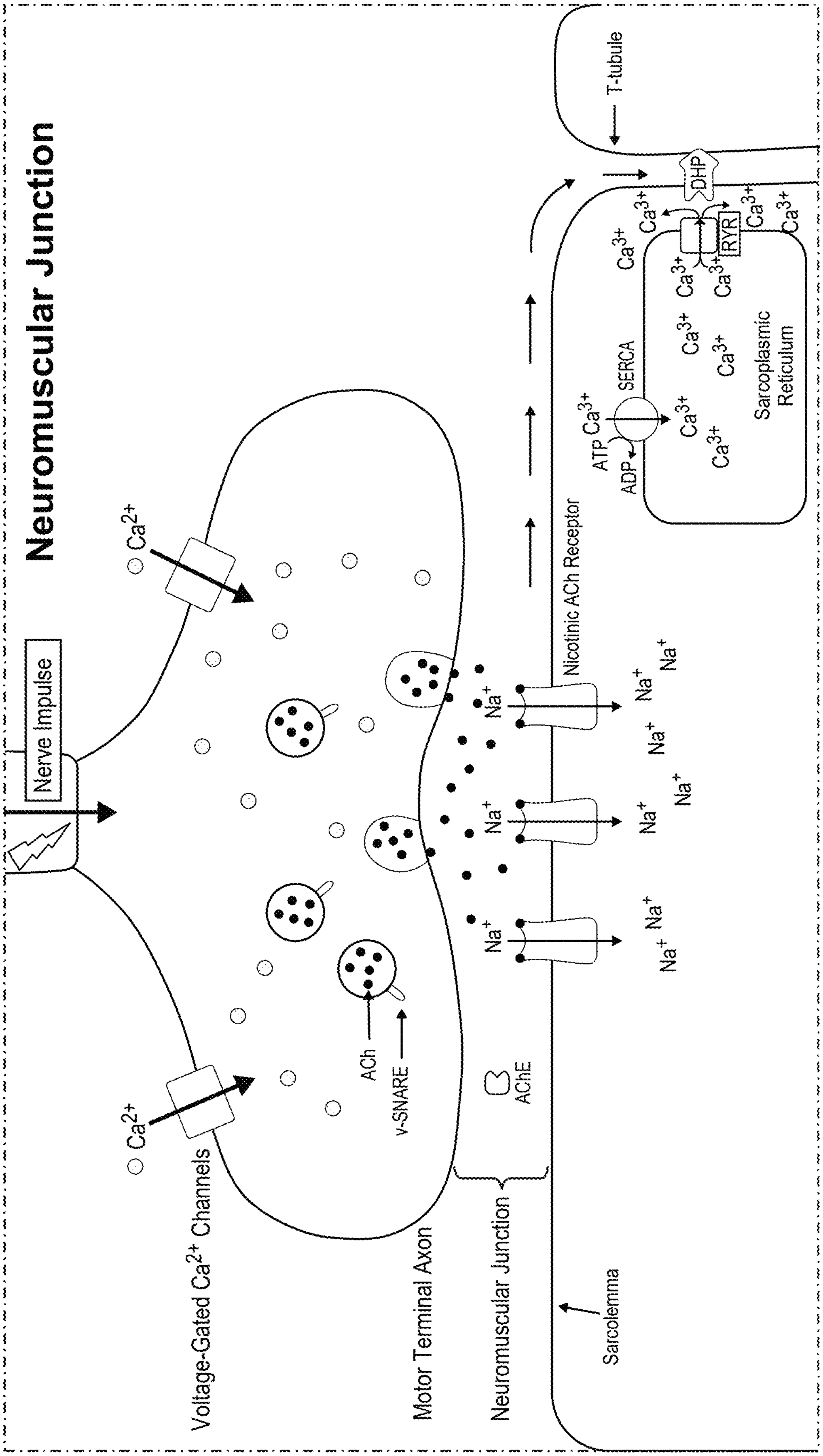
FIG. 1 schematically depicts an example neuromuscular junction.
Figure 2:
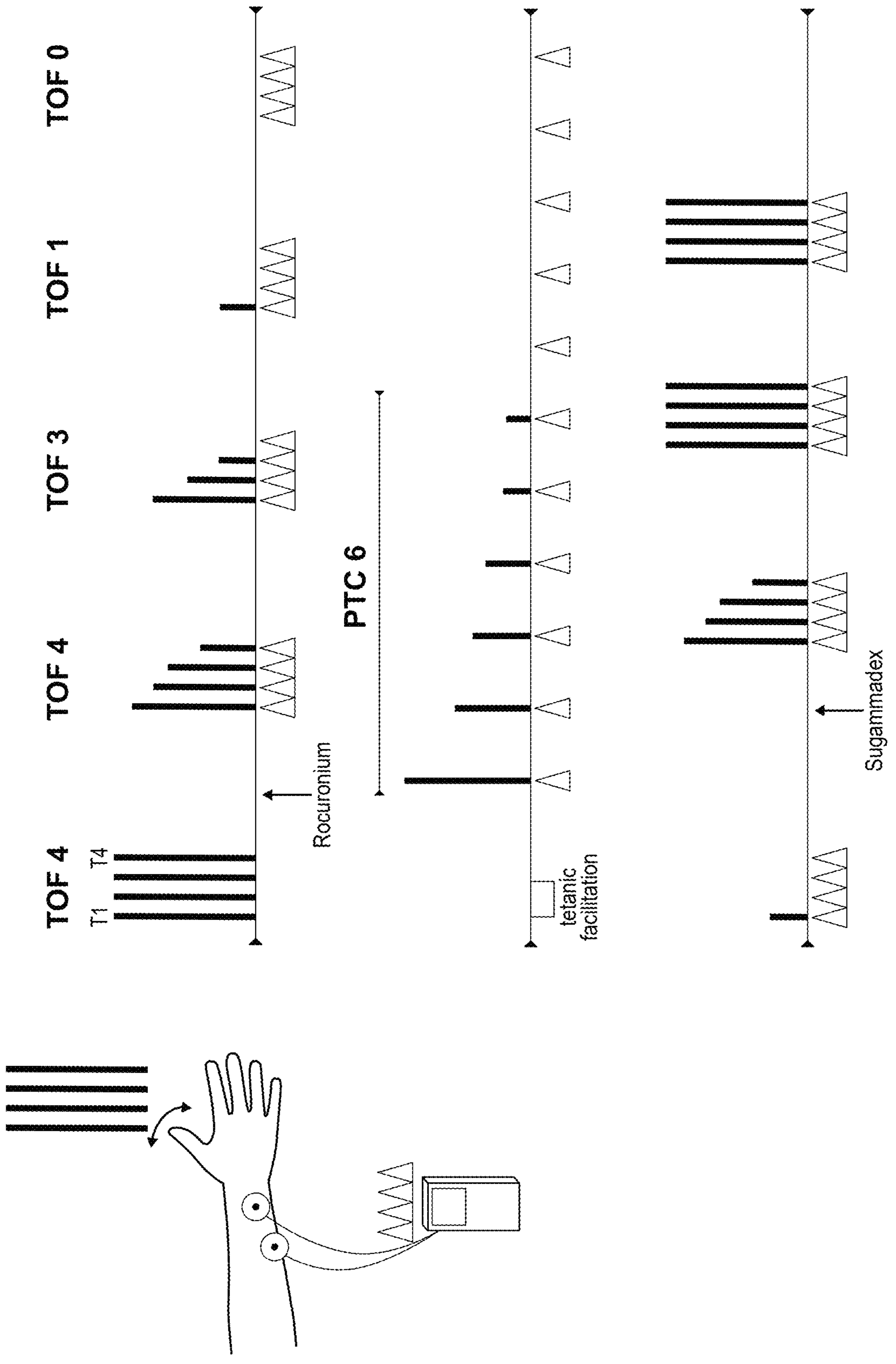
FIG. 2 shows examples of changes to TOF measurements, which may take place in some instances.

Certain example embodiments will now be described more fully hereinafter with reference to the accompanying drawings. The examples described and pictured herein should not be construed as being limiting as to the scope, applicability, or configuration of the present disclosure, unless explicitly claimed. Like reference numerals refer to like elements throughout the several views.

The terms "component," "module," and the like are intended to include and/or be implemented by a computer-related entity such as, for example, hardware, software, firmware, and/or combinations thereof. For example, a component or module may be a process running on a hardware processor such as a central processing unit (CPU), a processor, an object, an executable, a thread of execution, and/or a computer. By way of example, an application running on a computing device and/or the computing device can be a component or module. One or more components or modules can reside within a process and/or thread of execution, and a component/module may be localized on one computer and/or distributed between two or more computers (e.g., in two or more physically or wireless connected devices in a common location, across a network, etc.). In addition, these components can execute from various non-transitory computer readable media having various instructions and/or data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it will be appreciated that although this example is described in terms of separate modules corresponding to various functions performed, some examples may not necessarily use modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, and/or can be operably coupled to, processing circuitry to modify the behavior and/or capability of the processing circuitry based on the hardware and/or software that is added to or otherwise operably coupled to the processing circuitry to configure the processing circuitry accordingly. An operable coupling should be understood to relate to direct or indirect connection that, in either case, enables functional interconnection of components that are operably coupled to each other. The processing circuitry itself may refer to a hardware processor such as a CPU, application specific integrated circuit (ASIC), field programmable gate array (FPGA), and/or the like.

As used herein, the terms "neuromuscular block" and "neuromuscular blockade" are used interchangeably. Moreover, neuromuscular block/neuromuscular blockade may be thought of as being a type of paralysis induced by chemical (as in neuromuscular blocking agent) or mechanical (as by, for example, compression or vascular insufficiency) means.

In certain example embodiments, biophysiological signals are used to determine the density of a neuromuscular block objectively and quantitatively (instantaneously and/or over time), e.g., without reliance on patient feedback or actively stimulating the patient. As such the biophysiological signals may be used to determine the effectiveness of a chemically or mechanically effected neuromuscular block, in instances in which the patient is non-human and/or uncooperative but nonetheless still susceptible to such techniques. Example biophysiological signals that may be used in connection with certain example embodiments include, for example, heart rate, respiration rate, muscle movement, skin temperature, active or passive neurological activity, and/or the like. The biophysiological signals may be measured by various monitoring systems, which may be active or passive monitoring systems. These monitoring systems include, for example, sensors configured to generate signals based on electromyography (EMG) or acoustic myography (AMG), electrocardiogram (EKG) sensors, as well as accelerometers, Laser Doppler Vibrometers (LDV), interferometers, temperature detectors, magnetometers, and/or the like.

In certain example embodiments, spontaneous muscle movement may be measured, for example, by an EMG. The muscle movement measurements may be analyzed (e.g., in a frequency domain), and a determination of an effectiveness of an anesthetic may be determined based on, for example, the power of the muscle movement measurements in the frequency domain. In certain example embodiments, additional signals from different types of sensors may provide further information to a clinician relating to the status of the patient being monitored that may, for example, inform on spontaneous muscle movement or another aspect of the patient being monitored.

In certain example embodiments, a signal sensor set may indicate the effect at, or remote from, the location of the sensor. Different effects of neuromuscular block effect/density may occur in different sensor locations owing to, for example, maturity of the neuromuscular junction, the density of the neuromuscular connections, the mass or density of the muscular tissue underlying the sensors, etc. Thus, in certain example embodiments, it may be advantageous to measure biophysiological signals at a plurality of different locations, one of which might or might not correspond to an area of interest.

Signal processing techniques may be implemented to help condition the signal, e.g., by using high, low, and/or band-pass filters; amplifiers; application of a function or transform (e.g., a Fast Fourier Transform (FFT)); signal amplification; etc. In certain example embodiments, the analysis of the muscle movement may take place in the frequency domain. The analysis in the frequency domain may include, for example, plotting the average power in a frequency band of interest, e.g., spectral power, over time. Determining the average spectral power of the muscle movement measurements in a frequency band of interest over time in this example may be illustrative of the effectiveness of an anesthetic as inversely proportional to the power of the muscle movement measurements in the frequency band of interest. Similarly, as another example, changes in the variance of a signal measurement (e.g., changes in the variance of measured power) may inform on the degree of blockade in some instances and thus may be monitored in certain example embodiments. The gradient of the signal, gradient of in-band power, and/or other measures also may inform on the degree of blockade in some instances and thus may be monitored in certain example embodiments. In certain example embodiments, the muscle movement measurements may be received from a plurality of points on a patient's body and a neuromuscular block may be characterized based on a comparison of the muscle movement measurements in the frequency domain among these points, as a function of a plurality of signals from multiple sensors, and/or in some other manner.

It is noted that there may be a difference in the changes in signal from different groups of skeletal muscle. For example, using a signal taken from the temporalis muscle (temple of head [which is finer/thinner/less mass]) may reveal changes differently than the vastus (thigh) muscle [which is much larger/denser]. It will be appreciated that the changes identified may be changes in raw or processed signal amplitude, frequency, and/or the like. The differences noted may, in fact, be informative of neuromuscular blockade. Indeed, because the paralytic should have an effect throughout the body, one might expect the resultant measurement to be the same regardless of the measurement location, but that might not always be the case and instead there might be additional informative detail in the measurements taken from different sites. In a related regard, certain example embodiments thus may include a mapping of known surrogate sites where, for example, a measurement at a thumb muscle may inform about the neuromuscular blockade for laryngeal muscles.

Example Apparatus

Figure 3:
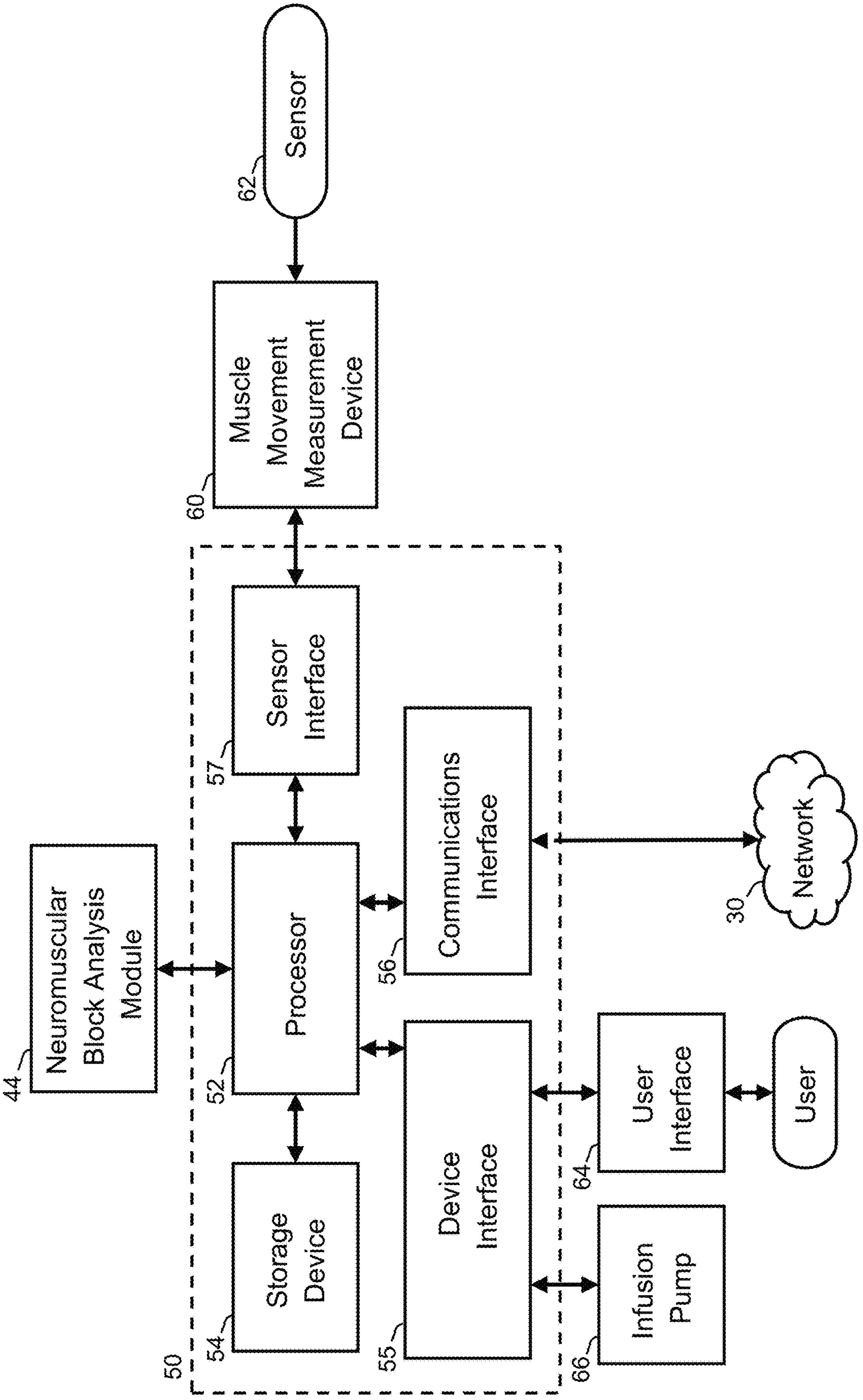
FIG. 3 is a block diagram of an example apparatus for neuromuscular block determination according to certain example embodiments.

FIG. 3 is a block diagram of an example apparatus for neuromuscular block determination according to certain example embodiments. The apparatus of FIG. 3 may be employed, for example, on a client, a computer, a network access terminal, a personal digital assistant (PDA), cellular phone, smartphone, network device, server, proxy, and/or the like. Alternatively, embodiments may be employed on a combination of devices. Accordingly, certain example embodiments may be embodied wholly at a single device or by devices that are connected together (e.g., in a client/server, distributed computing system, and/or other architectural relationship). Furthermore, it should be noted that the devices or elements described below may not be mandatory and thus some may be omitted in certain embodiments.

The FIG. 3 example apparatus is configured to determine an effectiveness of a neuromuscular block. In certain example embodiments, the apparatus may include or otherwise be in communication with processing circuitry 50 that is configured to perform data processing, application execution, and other processing and management services. In certain example embodiments, the processing circuitry 50 may include a storage device 54, a device interface 55, a communications interface 56, a sensor interface 57, and a processor 52 that may be in communication with or otherwise control, a neuromuscular block analysis module 44, a muscle movement measurement device 60, and a touchscreen or other display 64. As such, the processing circuitry 50 may be embodied as a circuit chip (e.g., an integrated circuit chip) configured (e.g., with hardware, software, firmware, or a combination thereof) to perform operations described herein. However, in certain example embodiments, the processing circuitry 50 may be embodied as a portion of a server, computer, laptop, workstation, one of various mobile computing devices, or other architectures. In situations where the processing circuitry 50 is embodied as a server or at a remotely located computing device, the user display 64 may be disposed at another device (e.g., at a computer terminal or client device) that may be in communication with the processing circuitry 50 via the device interface 55 and/or a network. The communications interface 56 may include one or more interface mechanisms for enabling communication with other devices and/or networks (e.g., network 30). The resolution and precision of the muscle movement measurement device 60 is very high and thereby produces high accuracy and highly precise quantitative information for the user.

The user interface 64 may be in communication with the processing circuitry 50 via the device interface 55 to receive an indication of a user input at the user interface 64 and/or to provide an audible, visual, mechanical or other output to the user. As such, the user interface 64 may include, for example, a keyboard, a mouse, a joystick, a display, a touchscreen, a microphone, a speaker, a cell phone, and/or other input/output mechanisms. In embodiments where the apparatus is embodied at a server or other network entity, for example, a local user interface 64 may be limited or even eliminated in some cases. As indicated above, the user interface 64 may be remotely located.

In some cases, the communications interface 56 may include any technology such as a device or circuitry embodied in either hardware, software, firmware, or a combination there that is configured to receive and/or transmit data from/to the network 30 and/or any other device or module in communication with the processor 52. In this regard, the communications interface 56 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Bluetooth, Wi-Fi, Ethernet or other methods. In situations where the communications interface 56 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In certain example embodiments, the storage device 54 may include one or more storage or memory devices such as, for example, volatile and/or non-volatile memory that may be either fixed or removable. The storage device 54 may be configured to store information, data, applications, instructions or the like for enabling the apparatus to carry out various functions in accordance with certain example embodiments. For example, the storage device 54 may be configured to buffer input data for processing by the processor 52. Additionally or alternatively, the storage device 54 may be configured to store instructions for execution by the processor 52. As yet another alternative, the storage device 54 may include one of a plurality of databases that may store a variety of files, contents or data sets, such as muscle movement measurements. Among the contents of the storage device 54, applications may be stored for execution by the processor 52 in order to carry out the functionality associated with each respective application.

The processor 52 may be embodied in a number of different ways. For example, the processor 52 may be embodied as a CPU, a microprocessor, or other processing element, a coprocessor, a controller or various other computing or processing devices including integrated circuits such as, for example, an ASIC, an FPGA, a hardware accelerator, and/or the like. In certain example embodiments, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to certain example embodiments when configured accordingly. Thus, for example, when the processor 52 is embodied as an ASIC, FPGA, or the like, the processor 52 may be specifically configured hardware for conducting the operations described herein. Alternatively, as another example, when the processor 52 may be embodied as an executor of software instructions, and the instructions may specifically configure the processor 52 to perform the operations described herein.

In certain example embodiments, the processor 52 (or the processing circuitry 50) may be embodied as, include, or otherwise control the neuromuscular block analysis module 44, which may be, for example, a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the neuromuscular block analysis module 44 as described below. In certain example embodiments, then, the neuromuscular block analysis module 44 may have the same or different structure as the processor 52, e.g., it may be implemented as hardware, software, firmware, or a combination thereof.

The neuromuscular block analysis module 44 may include tools to facilitate neuromuscular block analysis. In certain example embodiments, the neuromuscular block analysis module 44 may be configured to receive muscle movement measurements, analyze the muscle movement measurements (e.g., in a frequency domain), and determine an effectiveness of an anesthetic based on the analysis of the muscle movement measurements (e.g., in the frequency domain). The determination of effectiveness of the muscle movement measurements may be in real time or based on muscle movement measurements, stored in a memory, such as storage device 54.

The processing circuitry 50 may be in communication with the muscle movement measurement device 60. The muscle movement measurement device 60 may include an EMG sensor, AMG sensor, EKG sensor, accelerometer, strain gauge, laser vibrometer (e.g., an LDV), interferometer, temperature detector, magnetometer, microphone (e.g., spontaneous acoustomyogram), and/or the like. Although the examples herein are directed toward an embodiment in which the muscle movement measurement device is an EMG, one of ordinary skill in the art will appreciate that similar methods may be used for other muscle measurement devices, such as the examples listed above. Thus, in certain example embodiments, the neuromuscular block analysis module 44 may be configured to receive input from one or more different types of sensors.

In certain example embodiments in which the muscle movement device 60 is an EMG, the EMG may be in communication with a sensor 62, such as an electrode. The sensor 62 may be a single electrode or be a plurality of electrodes, and the electrode(s) may be unipolar. In certain example embodiments, the sensor 62 may be a needle electrode or an adhesive electrode. Utilization of multiple electrodes and/or needle electrodes may provide superior signal strength and clarity, inform as to a clinical gradient due to, for example, muscle mass, neural innervation, maturity, etc. By way of example, at least one sensor may be configured to generate an EMG or other signal and may comprise one or more adhesive measurement electrodes and/or one or more needle measurement electrodes. The sensors may be contact and/or non-contact sensors in different example embodiments. In one example, there may be two or more electrodes.

In certain example embodiments, the apparatus may include a link to an intelligent control/command to respond to reported data. For instance, this interface may be used to control administration of an NMBA, e.g., by controlling an infusion pump 66 or the like.

Doing so may be useful in attaining attain a target degree of blockade over time. As another example, the interface may be used to control a ventilator, e.g., to modify ventilation parameters using changes in muscle condition in connection with, for example, weaning the subject from mechanical ventilation. Other devices may be controlled for these and/or other purposes. In a similar vein, in certain example embodiments output from the apparatus may be provided to an external device (e.g., an infusion pump, ventilator, etc.) for that external device to interpret (e.g., to make an automated clinical decision), and accordingly provide or adjust a treatment or administration based on program logic from the external device itself.

In certain example embodiments, a neuromuscular block characterization system is provided. A muscle movement measurement device is configured to generate, unprompted by impulse stimulation to a subject from an external source (e.g., without impulse stimulation from an electromagnetic source (from an electric current or magnetic field), a mechanical source such as a reflex hammer (which might otherwise cause acute muscle stretch leading to reflex arc activation), direct or indirect external manipulation, etc.), at least one signal representative of muscle movement measurements at at least one location of a body of the subject while the subject is experiencing neuromuscular paralysis caused by biophysiological processes at neuromuscular synapses throughout the body including remote from the at least one location. A processing circuit is configured to run a neuromuscular block analysis module, with the module being configured to receive the at least one signal, analyze the muscle movement measurements embedded in the at least one signal, and determine a degree of neuromuscular blockade associated with the neuromuscular paralysis being experienced by the subject. The processing circuitry is further configured to generate, for display via a display device, an indication of the degree of the neuromuscular blockade at each said location on the body. This approach may be useful, for example, when the subject is experiencing neuromuscular paralysis caused by administration of a depolarizing or nondepolarizing agent, when the subject is experiencing neuromuscular paralysis caused by application of mechanical blocking means, and/or in other circumstances.

It will be appreciated that the techniques of certain example embodiments may be useful in characterizing active, subject-initiated movements (which are distinguishable from passive range of motion, e.g., initiated by a clinician, or sudden jerkiness). Clinicians may use the techniques of certain example embodiments to identify normally imperceptible micro-movements. Also of note is that it has been discovered that an EMG, for example, will identify the bioelectric potential signal in muscles, e.g., as the summation of at least (1) the electrical innervation from motor neurons, and (2) externally-applied mechanical displacement of the muscle. A spontaneous EMG, for example, is a biopotential signal of a muscle that is "at rest" and in essence is a "hum" of a muscle from miniscule nerve-muscle interactions not consciously commanded by the subject.

It also will be appreciated that the display can be real-time and/or an after-the-fact measurement on a device local to or remote from the subject. With respect to an after-the-fact display, the data from the real-time display may remain when the collection is complete, e.g., and the user can scroll back through or otherwise navigate "backwards in time" through the data. Additionally, or alternatively, the data from a collection may be recorded and played back. In this case, then, the signal(s) may be fed back to the processing circuit and, in such instances, these signals are derived from the recorded data rather than being derived "live" from the subject. This is represented in the FIG. 3 block diagram by the two-headed arrow between boxes 52 and 54. In certain example embodiments, the data being collected may be sent to the storage device. When post-processing, the data may be sourced from the storage device and sent to the processor.

Example Neuromuscular Block Determination

A patient may be injected with a neuromuscular blocking agent (NMBA, e.g., rocuronium) at, for example, an intravenous injection site. As the NMBA takes effect on the neuromuscular junction (and the resulting neuromuscular block), it may be measured using one or more sensors over one or more "relevant" muscles. In this sense, one or more sensors locations may be the same as or different from one or more areas of interest. The effects (e.g., character of the changes seen) of the neuromuscular block may relate to the characteristics of the nerve/muscle interface and the NMBA used to create the block. In certain example embodiments, the measurement points may be large muscles (e.g., vastus medialis) or small muscles (orbicularis oculus). In certain example embodiments, the effectiveness of the neuromuscular block may be described as block density or how "profound" the neuromuscular block is. Muscle movement (e.g., spontaneous non-obvious muscle movement or the "hum" described above) may be measured at the measurement locations. In certain example embodiments, the muscle movement measurements may be accomplished using an EMG.

Figure 4:
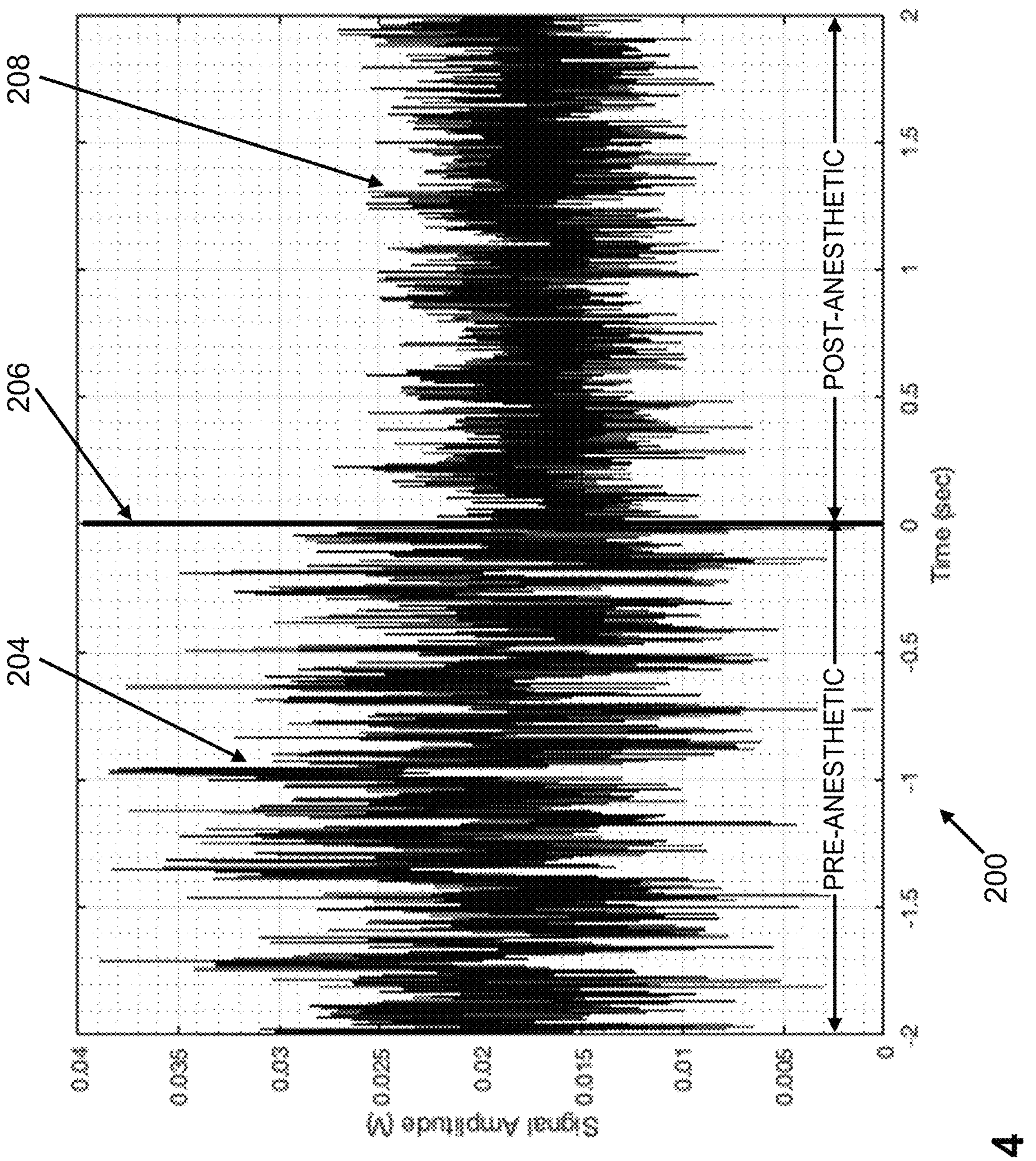
FIG. 4 is an example electromyograph according to certain example embodiments.

FIG. 4 is an example electromyograph according to certain example embodiments. An EMG sensor may be connected to one or more measurement points such as, for example, a surface overlying vastus medialis or adductor pollicis, on the patient. The EMG sensor may output an electromyograph 200, that is, the EMG sensor may record the signal as an electromyograph. In certain example embodiments, the muscle movement measurements may be analyzed in the time domain using the EMG signal level (EMG power level) as a function of time. The EMG signal may be used to distinguish the muscle movement measurements "at rest" and "active" (as with volitional movements). In certain example embodiments, the signal amplitude may be effective in distinguishing between at-rest and blocked EMG signal characteristics, both instantaneously and over time. In certain example embodiments, the signal amplitude may be effective in distinguishing between a complete block, graduations of lesser block, or regional differences in block.

As depicted in FIG. 4, the raw signal amplitude of the pre-anesthetic EMG signal 204, e.g., at rest, includes a significantly greater magnitude than the EMG signal post-NMBA administration 208. The neuromuscular blocking agent in the depicted example was administered at the time bar 206. In certain example embodiments, the native EMG signal 204, e.g., baseline, may be compared to the post-NMBA EMG signal 208 to determine a change in EMG signal. The change in EMG signal may be compared to a change threshold, such as predetermined value or percentage. A change in EMG signal that satisfies the change threshold may be determined to be an effective neuromuscular block, or a graduated degree of neuromuscular blockade. In certain example embodiments, the change in EMG signal may be compared to more than one change threshold or change threshold ranges to determine an effectiveness of the neuromuscular blockade, e.g., appropriate for the clinical condition.

Figure 5:
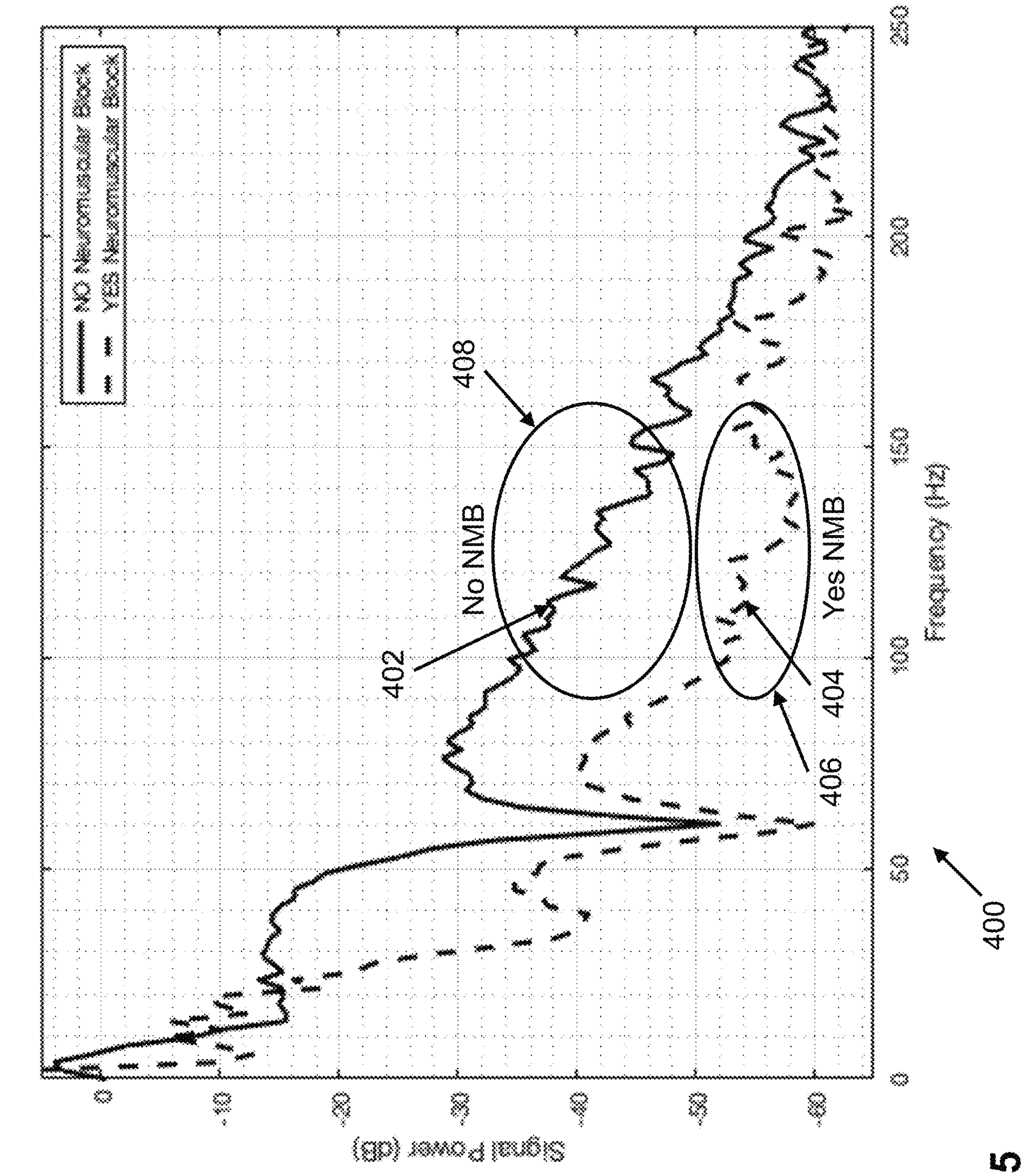
FIG. 5 is an example electromyogram in the frequency domain according to certain example embodiments.
Figure 6:
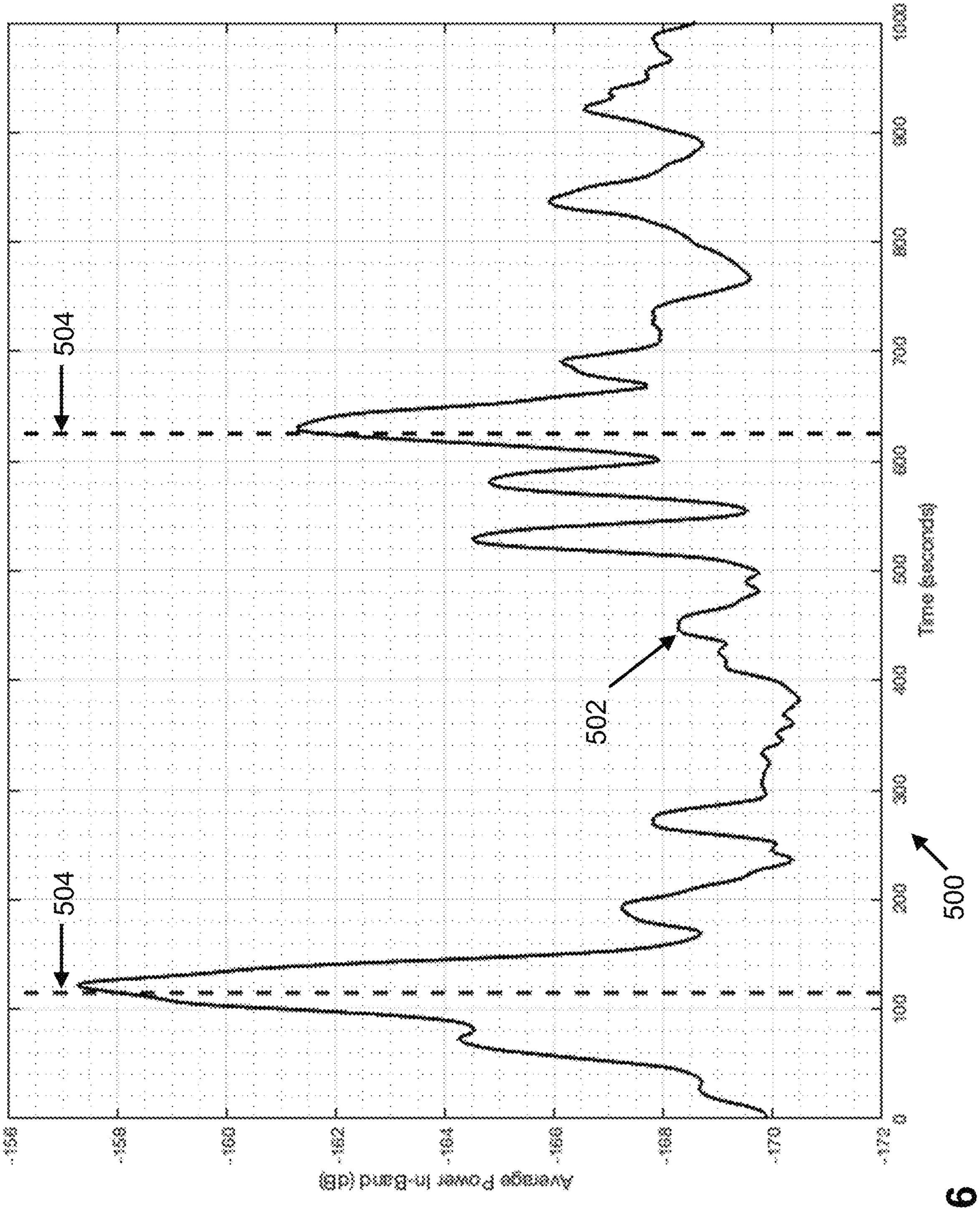
FIG. 6 is an example average pass-band spectral power plot over time of an electromyogram, in accordance with certain example embodiments.

FIGS. 5-6 illustrate an example analysis of an EMG signal received from a piglet to determine the effectiveness of a neuromuscular block anesthetic. In this study, one week old piglets were anesthetized with inhalational induction and maintenance with sevoflurane. Vascular access (intravenous and arterial vascular catheterization) was performed after endotracheal intubation with direct laryngoscopy. A single channel of an EMG monitor was applied using needle sensors (2 cm apart percutaneously) of the lower extremity (anterior thigh). Baseline signals were obtained. Administration of rocuronium was monitored continuously using the monitor and demonstrated prompt reduction in power/amplitude of the signal in the frequency range of 100-150 Hz. Upon return of signal, additional doses of rocuronium reduced signal power. Each time rocuronium was administered, the signal power reduced (which has been determined to be statistically significant at $p<0.05$).

In certain example embodiments, the EMG signal may be analyzed in the frequency domain. In this regard, FIG. 5 is an example electromyogram in the frequency domain 400 according to certain example embodiments. In certain example embodiments, a frequency domain method may be applied to the EMG signal, such as power spectral density by Fast Fourier Transform, ensemble averaging, or the like. Finite frequency bands, e.g., frequency bands of interest, may exhibit notable differences in power levels as a function of whether the muscle associated with the muscle movement measurement was affected by a neuromuscular block or not affected by a neuromuscular block. It is noted that the frequency band of interest may not be fixed, e.g., due to clinical condition(s) such as patient age, additional agents (e.g., volatile anesthetics), muscle mass sensed, human/non-human, etc.

The electromyogram in the frequency domain 400 includes frequency on the x-axis of 0-250 Hz and amplitude on the y-axis as a function of frequency (dB). The EMG signal in the frequency domain samples may be collected with a sampling rate of 2000/second and 16 bits of resolution. In certain example embodiments, the difference between the spectra of an EMG signal measured before and after administering the neuromuscular block is depicted. The pre-block EMG signals in the frequency domain 402 may be compared to the post-block EMG signals in the frequency domain 404. A post-block indication 406 is depicted by about a 15 dB decrease in the power level over the frequency band of approximately 100-150 Hz, compared to the pre-block EMG signal in the same frequency band 408. Lesser decreases may be observed both above and below this band. The clear difference in power in the 100-150 Hz frequency band may not be observed in other portions of the power spectrum. It also is noted that the post-block power level returns to pre-block power level values as the anesthetic block wears off over time, which may be consistent with the expected pharmacodynamics of the anesthetic.

As the degree of neuromuscular block changes over time (or more acutely with antagonist), the power increases to an initial baseline. The degree to which the power decreases and increases is related directly (but not necessarily linearly) to the degree of neuromuscular blockade effected.

In certain example embodiments, a band pass filter may be applied to the EMG signal to isolate the frequency of interest, such as 100-150 Hz, in the present example.

Additionally, the EMG signal over time, such as depicted in FIG. 4, may be frequency transformed. In certain example embodiments, the EMG signal over time may be frequency transformed by applying a 1024 point Fast Fourier Transform with successive transform windows that slide by 32 samples. The mean power in each frequency bin may be calculated as a function of time that corresponds to the EMG signal over time. The mean of the power in the frequency bins may correspond to the frequency band of interest, such as 100-150 Hz in the present example. The output of the frequency transform may be the average spectral power (ASP) plotted over time 500 as depicted in FIG. 6.

FIG. 6 is an example average pass-band spectral power plot over time of an electromyogram, in accordance with certain example embodiments. The average spectral power plotted over time is represented by signal 502 and may include administration of the NMBA rocuronium 504.

In the example depicted, in FIG. 6, the y-axis is the average spectral power in the 100-150 Hz band in a range of about −157 to about −171 dB, and the x-axis is time 0-1000 seconds. A paralytic anesthetic is shown to be administered two times; rocuronium is administered at ~115 seconds and ~625 seconds, as depicted by time bars 504. Upon each administration of rocuronium (a neuromuscular blocking agent), there is a clear and distinct change (reduction) in power at the selected frequency band indicating an objective measure of the changes (that is, blockade of the transmission of signal across the neuromuscular endplate/synapse) in muscular tone.

The effectiveness of a neuromuscular block may be determined based on the analysis of the muscle movement (the "hum" described above) in the frequency domain. In certain example embodiments, the ASP plot 500 may be displayed, such as on user interface 64. Additional or alternatively, an ASP value based on the ASP plot may be displayed. In certain example embodiments, historical ASP data based on the patient, like patients, the anesthetic or the like may be used to determine an ASP value indicative of an effective neuromuscular block. A clinician may use the ASP plot 500 or ASP value indicative of an effective neuromuscular block to manually determine the effectiveness the anesthetic based on changes in the ASP over time or based on a predetermined ASP value.

In certain example embodiments, the effectiveness of the NMBA may be determined automatically, and potentially on a repeated or continuous basis, such as by the processing circuitry 50. In certain example embodiments, the pre-anesthetic ASP (e.g., at approximately 115 seconds and 625 seconds of the signal 502) may be compared to the post-NMBA ASP (e.g., at approximately 150 seconds and 665 seconds of the signal 502) to determine an ASP change. The ASP change may be compared to a predetermined ASP change threshold, such as a pre-determined change value or percentage of the pre-anesthetic ASP. In certain example embodiments, the ASP change threshold may be 7 dB, an ASP change which satisfies the ASP change threshold may be determined to be an effective neuromuscular block, and an ASP change which fails to satisfy the ASP change threshold may be determined to be an inadequate (or failed) neuromuscular block.

In certain example embodiments, the pre-anesthetic ASP and post-NMBA ASP may be compared in real time. In one such example embodiment, a "control" area (e.g., a limb isolated using a tourniquet) may be designated on a patient, which will not be exposed to neuromuscular blocking agent. Muscle movement measurements of the control area, such as a leg not undergoing a medical procedure, may be utilized to determine a pre-anesthetic ASP. The post-NMBA ASP may be determined from the muscle movement measurements of the area in which the anesthetic is applied, such as a second leg undergoing the medical procedure. This technique in essence can be used to show a non-blocked neuromuscular junction by applying a tourniquet to a limb (thus blocking the circulation of blood and the distribution of neuromuscular blocking agent to that limb). In this case, the limb is not "exposed" to neuromuscular blocking agent and will continue to exhibit electromyography signal consistent with active neuromuscular activity as compared with the rest of the body (no or reduced neuromuscular activity).

In some example embodiments, a second ASP change threshold may be set based on a predetermined level of effective neuromuscular block. The second ASP change threshold may be used to determine when anesthetic is wearing off prior to the neuromuscular block not being effective or clinically advantageous. In certain example embodiments, the second ASP change threshold may be set at 5 dB above the lowest ASP value after satisfying the ASP change threshold, which may be the initial decrease in ASP after administering the anesthetic. In certain example embodiments, one or more additional ASP change thresholds may be used to determine the effectiveness of the neuromuscular block. Thresholds in the range of, for example, 2-50 dB, or 3-40 dB, or 5-30 dB, may be used in certain example embodiments. Although, discussed in the context of automatic determinations, a technician may use the ASP change thresholds or similar thresholds in the manual determination of the effectiveness of the anesthetic.

In certain example embodiments, the muscle movement measurements may be taken at a plurality of points on the patient such as, for example, the vastus medialis [thigh], biceps brachialis [upper arm], orbicularis oculus [eye], etc. In certain example embodiments, the analysis of the muscle movement measurements in the frequency domain, as discussed above, may be performed on muscle movement measurements at each of the respective points on the patient. The muscle movement measurements may be compared in the frequency domain to determine the level and density of the neuromuscular block. The comparison of the muscle movement measurements in the frequency domain may be used, for example, to determine the relative block density related to muscle mass, neuromuscular innervation density, neurodevelopmental characteristics, or effect of co-administered agents (e.g., aminoglycosides).

Additionally or alternatively, an ASP associated with a muscle movement measurement may be compared to the ASP value indicative of an effective neuromuscular block to determine an ASP value difference. The ASP value difference may be compared to the ASP difference threshold, in a manner substantially similar to the ASP change threshold discussed above.

In certain example embodiments, the location and density of the neuromuscular block based on the ASP change thresholds or ASP value difference threshold may be displayed on the user interface 62 as color or shade code or a body outline or portion thereof. In certain example embodiments, an effective block may be indicated as green and an ineffective or failed block indicated as red. In certain example embodiments, other shades may be used to indicate effect or densities associated with the particular location and the dynamic changes that occur over time. This technique may be useful, for example, to show a difference in degree of block at each sensed site.

As noted above, signal conditioning functions may be applied in certain example embodiments. These signal conditioning functions may include, for example, the application of one or more filters applied on a raw signal (e.g., high, low, and/or bandpass filters), the use of an amplifier on the raw signal (e.g., prior to application of a bandpass or other filter), application of a transformation (e.g., to transform the signal from the time domain to the frequency domain), and/or the like.

In general, certain example embodiments may seek to identify block-indicative markers in a number of different ways. As described above, analysis in the time and/or frequency domain may be used to identify such block-indicative markers. That is, block-indicative markers may be magnitude changes greater than a threshold such as, for example, magnitude changes that are coincident, within a predetermined time period, of administration of a neuromuscular blocking agent. Other techniques for identifying block-indicative markers may be used, additionally or in the alternative. These other techniques include, for example, the use of an artificial intelligence (AI) or machine learned approach, root mean square analysis, peak/trough identification, wavelet transformation, etc.

Root mean square analysis refers to a statistical method that generates data points representing the average magnitude of fluctuations within the data, independent of the sign of the data. Peak/trough identification refers to an analytic method that generates data points representing the magnitude of the maximum excursion of the signal. Wavelet transformation is a form of analysis in the frequency domain, but instead of decomposing the signal into characteristic sinusoids, the characteristic signals are orthogonal functions. It will be appreciated that these and/or other signal decomposition techniques may be used in different example embodiments and that power-like differences may reveal the degree of neuromuscular blockade regardless of the signal processing technique used.

An AI or machine learning (ML) approach to identifying potential markers of interest may be used in certain example embodiments. An appropriate model (e.g., a neural network (NN), convolution neural network (CNN), naïve Bayesian network (NBN) or the like) may be trained, and then data from one or more sensors may be provided to the model to indicate the degree of neuromuscular blockade. To train the model, training data may be provided. The training data may be provided from a subject patient, a library of prior subjects, etc. Training data may include signals from one or more sensor types. Labels on the training data may indicate the type and/or placement of sensor(s), demographic data about the subject, an indication of the degree of neuromuscular blockade (e.g., as determined via TOF or other analysis), whether and what NMBAs have been applied, etc. The trained model may be prompted as new data streams in, either periodically or continuously, e.g., to provide an indication of an extent of blockade. Further clinical observations may be used to refine the model over time. It will be appreciated that certain example embodiments may use multiple models or model stacks, e.g., to quantify the degree of blockade and to associate a degree of confidence with the thus-quantified degree of blockade.

As indicated above, multiple measurements may be taken, regardless of how and where those measurements might be taken. Thus, in certain example embodiments, the muscle movement measurement device 60 may be configured to generate a plurality of signals for multiple locations of the body. For example, one type of sensor may take measurements at multiple locations or multiple types of sensors may take measurements at the same or different locations.

In a similar vein, the muscle movement measurement device 60 may be connected to at least one sensor provided remote from the at least one location from which data is drawn. In this sense, the sensor(s) may be “clinically” remote (and thus relate to a surrogate measurement) and/or “technically” remote (and thus be located in a non-contact area). For the latter, a remote sensor may be one that is not in physical contact with the subject. For instance, an LDV is a stand-off, optical motion measurement sensor that can make the requisite muscle motion measurements but does not necessarily contact the subject. Likewise, a magnetometer can make EMG-equivalent measurements in at least some configurations and instances but does not need to be in contact with a subject patient.

With respect to the notion of a clinically remote sensor, each location for which at least one signal representative of muscle movement measurements is generated may be an area of observational interest, and the muscle movement measurement device 60 may be connected to at least one sensor that is provided remote from, and monitors an area other than, the area(s) of observational interest. In some instances, the area(s) of observational interest may correspond to an area of the subject to be operated on. In this regard, at least one location from which a muscle movement measurement is taken may be selected based on a predefined surrogate mapping that indicates which signals from which surrogate locations inform on different areas of interest on the human body. For example, the surrogate mapping may indicate that a signal taken by the muscle measurement device from the anterior thigh informs on the neuromuscular blockade of the larynx. The surrogate mapping may link each different area of interest to at least one surrogate location. In some instances, each link in the surrogate mapping may associate muscles of different character with one another such that, for each link, the surrogate location(s) pertain(s) to a muscle or muscles larger than, longer than, or having a different constituency than a muscle at the corresponding area of interest. In some instances, for each link in the surrogate mapping, analysis of muscle movement measurements embedded in signals obtained for the surrogate location(s) may indicate a magnitude change greater than a threshold signifies a change in neuromuscular blockade at the area of interest associated with the link. It will be appreciated that different thresholds may be determined, e.g., to signify differing changes in the amount of neuromuscular block. This information may be included in the surrogate mapping in certain example embodiments. In certain example embodiments, the choice of the surrogate location that is used for measurement may be optimized or otherwise specially selected for the muscle of interest. In some cases, larger or longer muscles may provide better a signal-to-noise ratio (SNR) compared to a smaller or shorter muscle, and thus the former may be preferred to the latter and thus used in a surrogate mapping. In other cases, a smaller or shorter muscle may be more convenient to access while still adequately and accurately informing on a larger or longer muscle and thus may be preferred and used in a surrogate mapping. In still other cases, some muscles may be difficult to access (e.g., the larynx may not be directly accessible because it is located behind other muscles), so a surrogate may be used.

Taking a measurement at other locations remote from an area where neuromuscular block is induced may be useful in other contexts as well. For example, in the case of electroconvulsive therapy (ECT), a tourniquet can be used to prevent the neuromuscular agent from reaching tissue distal to the tourniquet. This permits the limb to move when all other parts of body are blocked (and limp). Thus, in the case of ECT, the body is paralyzed except for the limb distal to the tourniquet and, as a result, when the induced seizure occurs, the brain signals show seizure, the body is limp, and the tourniquetted-limb (e.g., a foot for example) moves rhythmically in concert with the EEG signal seizure. The techniques disclosed herein thus may be useful in cases where there is a desire to provide a clinical "control" as in the case of, for example, ECT, and/or to compare two (or more) different areas including the control to thereby provide a relative assessment.

Regardless of whether the locations are clinically remote and/or technically remote, the location(s) of the sensor(s) may be selected based on neurologic input, endplate number, muscular volume, and/or a signal emitted from a muscle of interest. It is noted that some or all of these and/or other factors also may be taken into account in the determination of the degree of neuromuscular blockade. In certain example embodiments, the location(s) at which muscle movement measurements is/are taken may be "clinically" remote from an injection site of a neuromuscular blocking agent administered to the subject.

Example Neuromuscular Block Determination Flowchart

Figure 7:
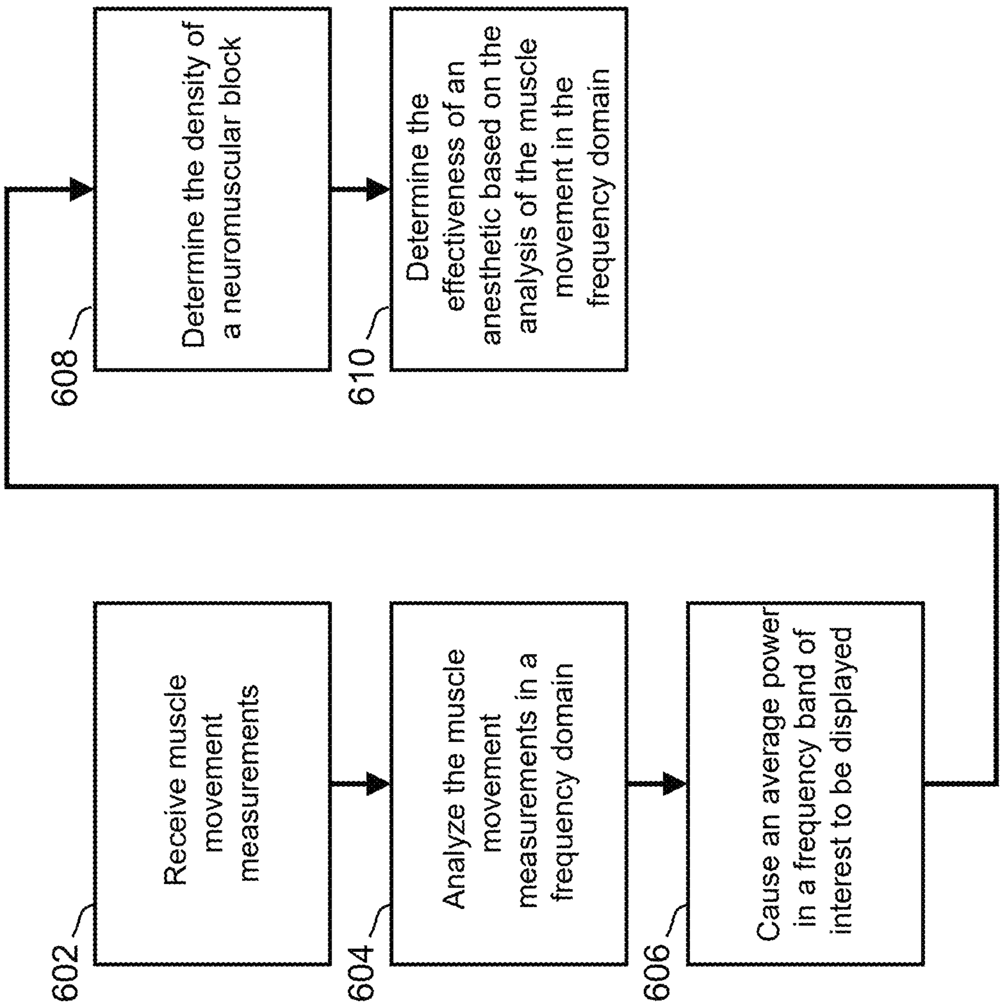
FIG. 7 is a flowchart showing an example method for neuromuscular block determination from data in the frequency domain, according to certain example embodiments.

From a technical perspective, the neuromuscular block analysis module 44 described above may be used to support some or all of the operations described above. The apparatus described in FIG. 3, for example, may be used to facilitate the implementation of several computer program and/or network communication based interactions. As an example, FIG. 7 is a flowchart of a method and program product according to certain example embodiments. It will be understood that each block of the flowchart, and combinations of blocks in the flowchart, may be implemented by hardware, firmware, processor, circuitry, and/or other devices associated with execution of software including one or more computer program instructions. For example, one or more of the procedures described above may be embodied by computer program instructions. In this regard, the computer program instructions that embody the procedures described above may be stored by a memory device of a user terminal and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to certain example embodiments is shown in FIG. 7. The method may be employed for neuromuscular block determination. The method may include, for example, receiving muscle movement measurements, at operation 602. The method may also include analyzing the muscle movement measurements in a frequency domain, at operation 604. At operation 610, the method may include determining an effectiveness of an anesthetic based on the analysis of the muscle movement in the frequency domain. The analysis at operation 604 and the determination at operation 610 may be aperiodic or continuous.

In certain example embodiments, the method may optionally include causing an average power in a frequency band of interest to be displayed, at operation 606. The method may optionally include determining the density of a neuromuscular block, at operation 608.

As will be appreciated from the above, a variety of visualizations may be provided. Generally, the visualizations may include categorical (e.g., red/green, blocked/unblocked, etc.) and/or continuous (e.g., numeric, percentage, etc.) output. By way of example, the degree of neuromuscular blockade may be determined as being one of two binary options, e.g., with the two binary options being indicative of blocked and non-blocked assessments, respectively. As another example, the degree of neuromuscular blockade may be determined as being a value on a scale, such as a numeric scale, percentage scale, or color-coded scale. In still another example, the degree of neuromuscular blockade may be indicated on a plot providing values for the subject over time. In certain example embodiments, muscle movement measurements may include with respect to the administration of NMBA, pre-block and post-block muscle movement measurements, and the neuromuscular block analysis module 44 may be further configured to compare the pre-block muscle movement measurements to the post-block muscle movement measurements, e.g., and send the output to a display.

Figure 8:
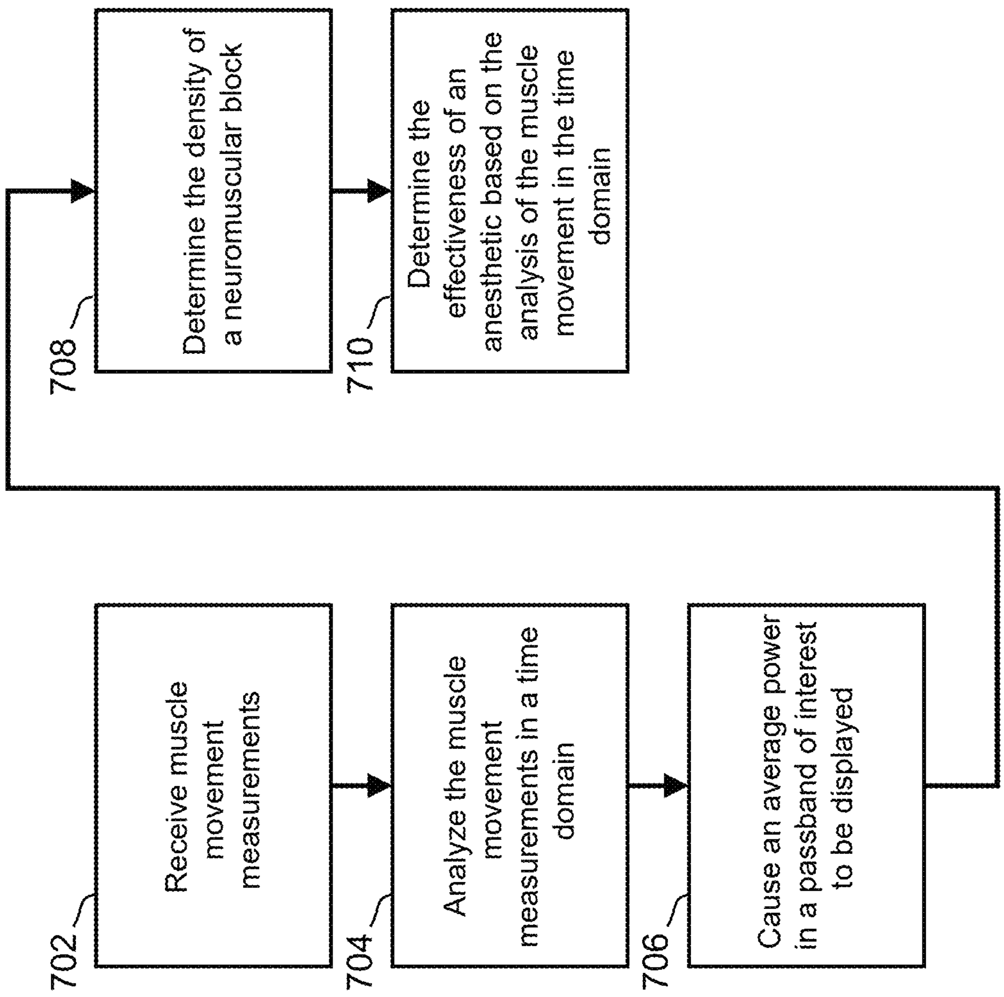
FIG. 8 is a flowchart showing an example method for neuromuscular block determination from data in the time domain, according to certain example embodiments.

FIG. 8 is similar to FIG. 7 in that FIG. 8 is a flowchart showing an example method for neuromuscular block determination from data in the time domain, according to certain example embodiments. More particularly, operations 602-610 in FIG. 7 generally match with operations 702-710 in FIG. 8, except that FIG. 8 involves analyzing muscle movement measurements in a time domain (operation 704), causing an average power in a passband of interest to be displayed (operation 706), and determining the effectiveness of an anesthetic based on the analysis of the muscle movement in the time domain (operation 710).

In certain example embodiments, an apparatus for performing the method of FIGS. 7-8 above may comprise a processor (e.g., the processor 52) or processing circuitry configured to perform some or each of the operations (602-610 and 702-710) described above. The processor may, for example, be configured to perform the operations (602-610 and 702-710) by performing hardware implemented logical functions, executing stored instructions, or executing algorithms for performing each of the operations. In certain example embodiments, the processor or processing circuitry may be further configured for additional operations or optional modifications to operations 602-610 and 702-710. In this regard, in certain example embodiments, the analysis of the muscle movement measurements in the frequency domain and the analysis of the muscle movement measurements in the time domain also include causing an average power in a frequency or other band of interest to be displayed. In certain example embodiments, the muscle movement measurements are received from an electromyogram sensor. In certain example embodiments, the electromyogram sensor includes adhesive measurement electrodes or needle measurement electrodes. In certain example embodiments, the electromyogram comprises at least two electrodes. In certain example embodiments, the electromyogram comprises at least one unipolar and/or bipolar electrodes. In certain example embodiments, the muscle movement measurements are received from an accelerometer, a laser vibrometer, or microphone. In certain example embodiments, the processing circuitry is further configured to apply a band pass filter to the muscle movement measurements. In certain example embodiments, the band pass filter is configured to pass frequencies of about 100-150 Hz.

Although certain example embodiments relate to depolarizing or nondepolarizing agent, the techniques disclosed herein may be used in connection with other types of agents that, perhaps more generally, cause weakness of muscle signal. Such agents include, for example, magnesium, dantrolene, and others. In a similar vein, the techniques disclosed herein may be used in connection with clinical conditions such as hypocalcemia, actin-myosin myopathies, and the like. For example, some clinical conditions (e.g., botulism) may mimic the administration of an NMBA, and the techniques disclosed herein may be used to determine the degree of neuromuscular block associated with the same.

In certain example embodiments, a neuromuscular block characterization system is provided. A muscle movement measurement device is configured to generate, unprompted by impulse stimulation to a subject from an external source, at least one signal representative of muscle movement measurements at at least one location of a body of the subject while the subject is experiencing neuromuscular paralysis caused by biophysiological processes at neuromuscular synapses throughout the body including remote from the at least one location. A processing circuit is configured to run a neuromuscular block analysis module, the module being configured to receive the at least one signal, analyze the muscle movement measurements embedded in the at least one signal, and determine a degree of neuromuscular blockade associated with the neuromuscular paralysis being experienced by the subject. The processing circuitry is further configured to generate, for display via a display device, an indication of the degree of the neuromuscular blockade at each said location on the body.

In certain example embodiments, a system comprises a transducer configured to generate a signal indicative of muscle movements of a body part unprompted by stimulation from an external source. The system is configured to generate an indication of neuromuscular blockade based on the signal generated by the transducer, the indication reflecting a degree of neuromuscular blockade affecting the body part.

In addition to the features of either of the two previous paragraphs, in certain example embodiments, the muscle movement measurement device may be connected to one or more contact and/or non-contact sensors. For instance, the sensor(s) may be configured to generate an EMG signal, an AMG signal, and/or the like; the sensors may include a magnetometer, an accelerometer, an EKG sensor, LDV, interferometer, temperature sensor, and/or the like; etc. In some instances, the neuromuscular block analysis module may be further configured to receive input from one or more different types of sensors. In some instances, the at least one sensor may comprise adhesive measurement electrodes and/or needle measurement electrodes; one or more electrodes which may or may not be unipolar electrode; etc., e.g., in the case where the at least one sensor is configured to generate an EMG or other signal.

In addition to the features of any of the three previous paragraphs, in certain example embodiments, the muscle movement measurement device may be configured to generate a plurality of signals for multiple locations of the body. That is, in certain example embodiments, at least one signal in the plurality of signals may be generated for each of the multiple locations of the body. In some cases, one signal may be generated for each of plurality of different locations (e.g., one signal for an arm muscle and one signal for a leg muscle), whereas multiple signals may be generated for each of plurality of different locations (e.g., multiple signals for an arm muscle and multiple signals for a leg muscle) in other cases.

In addition to the features of any of the four previous paragraphs, in certain example embodiments, the muscle movement measurement device may be connected to at least one sensor provided remote from the at least one location.

In addition to the features of any of the five previous paragraphs, in certain example embodiments, each said location for which the at least one signal representative of muscle movement measurements is generated may be an area of observational interest, and the muscle movement measurement device may be connected to at least one sensor that is provided remote from, and monitors an area other than, the area(s) of observational interest. The area(s) of observational interest may, for example, correspond(s) to an area of the subject to be operated on.

In addition to the features of any of the six previous paragraphs, in certain example embodiments, the at least one location may be selected based on a predefined surrogate mapping that indicates which signals from which surrogate locations inform on different areas of interest on the human body. That is, in some instances, the surrogate mapping may link each different area of interest to at least one surrogate location. For instance, the surrogate mapping may indicate that a signal taken by the muscle measurement device from the anterior thigh informs on the neuromuscular blockade of the larynx. In some instances, each link in the surrogate mapping may associate muscles of different character with one another such that, for each link, the surrogate location(s) pertain(s) to a muscle or muscles larger than, longer than, or having a different constituency than a muscle at the corresponding area of interest. In some instances, for each link in the surrogate mapping, analysis of muscle movement measurements embedded in signals obtained for the surrogate location(s) indicating a magnitude change greater than a threshold may be understood to signify a change in neuromuscular blockade at the area of interest associated with the link.

In addition to the features of any of the seven previous paragraphs, in certain example embodiments, the location(s) may be selected, and/or the determination of the degree of neuromuscular blockade may be made, based on neurologic input, endplate number, muscular volume, and/or a signal emitted from a muscle of interest In addition to the features of any of the eight previous paragraphs, in certain example embodiments, the location(s) may be remote from an injection site of a neuromuscular blocking agent administered to the subject.

In addition to the features of any of the nine previous paragraphs, in certain example embodiments, the subject may be experiencing neuromuscular paralysis caused by administration of a depolarizing or nondepolarizing agent, a clinical condition mimicking administration of a depolarizing or nondepolarizing agent, application of mechanical blocking means, and/or for some other reason.

In addition to the features of any of the 10 previous paragraphs, in certain example embodiments, the analysis of the muscle movement measurements embedded in the at least one signal may include identification of block-indicative markers in a frequency band of interest. For instance, the block-indicative markers may be magnitude changes greater than a threshold; the magnitude changes may be coincident, within a predetermined time period, of administration of a neuromuscular blocking agent; etc. In some instances, the analysis of the muscle movement measurements embedded in the at least one signal may include applying a FFT or other transform to convert the signal to the frequency domain.

In addition to the features of any of the 11 previous paragraphs, in certain example embodiments, the analysis of the muscle movement measurements embedded in the at least one signal may include application of a bandpass or other filter, with or without amplification, and optionally identification of block-indicative markers in the time domain.

In addition to the features of any of the 12 previous paragraphs, in certain example embodiments, the neuromuscular block analysis module may be implemented fully or partly in software; fully in partly in hardware, such as an FPGA or ASIC; and/or the like.

In addition to the features of any of the 13 previous paragraphs, in certain example embodiments, the degree of neuromuscular blockade may be determined as being one of two binary options, e.g., with the two binary options being indicative of blocked and non-blocked assessments, respectively; as being a value on a scale, such as a numeric scale, percentage scale, or color-coded scale; etc. In some instances, the degree of neuromuscular blockade may be indicated on a plot, e.g., providing values for the subject over time. The neuromuscular block analysis module may, for example, be further configured to cause an average power associated with the muscle movement measurements in a frequency band of interest to be displayed on a user interface.

In addition to the features of any of the 14 previous paragraphs, in certain example embodiments, the processing circuitry may be further configured to provide a control signal to control administration of a neuromuscular blocking agent. For instance, the control signal may be provided to an infusion pump or other device.

In addition to the features of any of the 15 previous paragraphs, in certain example embodiments, the muscle movement measurements may include pre-block and post-block muscle movement measurements, and the neuromuscular block analysis module may be further configured to compare the pre-block muscle movement measurements to the post-block muscle movement measurements. In addition to the features of any of the 15 previous paragraphs, in certain example embodiments, the neuromuscular block analysis module may be further configured to compare the muscle movement measurements to a first predetermined muscle movement value.

In certain example embodiments, a method of characterizing neuromuscular block is provided. The method may include the features of any of the 16 previous paragraphs. In a similar vein, in certain example embodiments, a program corresponding to these and/or other methods may be provided. Likewise, in certain example embodiments, there is provided a non-transitory computer readable storage medium tangibly storing a program that, when executed, causes a processor to perform operations corresponding to these and/or other methods.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe example embodiments in the context of certain exemplary combinations of elements and/or functions, it will be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits, or solutions to problems are described herein, it should be appreciated that such advantages, benefits, and/or solutions may be applicable to some example embodiments, but not necessarily all example embodiments. Thus, any advantages, benefits or solutions described herein should not be thought of as being critical, required, or essential to all embodiments or to that which is claimed herein.

What is claimed is:

1. A neuromuscular block characterization system, comprising:

a muscle movement measurement device configured to generate, unprompted by impulse stimulation to a subject from an external source, at least one signal representative of muscle movement measurements at at least one location of a body of the subject while the subject is experiencing neuromuscular paralysis caused by biophysiological processes at neuromuscular synapses throughout the body including remote from the at least one location; and processing circuitry configured to run a neuromuscular block analysis module, the module being configured to receive the at least one signal, analyze the muscle movement measurements embedded in the at least one signal, and determine a degree of neuromuscular blockade associated with the neuromuscular paralysis being experienced by the subject based on the analysis, wherein the processing circuitry is further configured to generate, for display via a display device, an indication of the degree of the neuromuscular blockade at each said location on the body, wherein the at least one location is selected based on a predefined surrogate mapping that indicates which signals from which surrogate locations inform on different areas of interest on the human body, and wherein the processing circuitry is further configured to provide a control signal to control administration of a neuromuscular blocking agent based on the determined degree of the neuromuscular blockade at each said location on the body.

2. The system of claim 1, wherein the muscle movement measurement device is connected to one or more contact and/or non-contact sensors, and the sensor(s) is/are configured to generate an electromyography (EMG) signal.

3. The system of claim 1, wherein the muscle movement measurement device is configured to generate a plurality of signals for multiple locations of the body, such that at least one signal in the plurality of signals is generated for each of the multiple locations of the body.

4. The system of claim 1, wherein each said location for which the at least one signal representative of muscle movement measurements is generated is an area of observational interest, and wherein the muscle movement measurement device is connected to at least one sensor that is provided remote from, and monitors an area other than, the area(s) of observational interest.

5. The system of claim 1, wherein the surrogate mapping links each different area of interest to at least one surrogate location.

6. The system of claim 5, wherein each link in the surrogate mapping associates muscles of different character with one another such that, for each link, the surrogate location(s) pertain(s) to a muscle or muscles larger than, longer than, or having a different constituency than a muscle at the corresponding area of interest.

7. The system of claim 5, wherein for each link in the surrogate mapping, analysis of muscle movement measurements embedded in signals obtained for the surrogate location(s) indicating a signal change greater than a threshold signifies a change in neuromuscular blockade at the area of interest associated with the link.

8. The system of claim 1, wherein the determination of the degree of neuromuscular blockade is based on neurologic input, endplate number, muscular volume, and/or a signal emitted from a muscle of interest.

9. The system of claim 1, wherein the location(s) is/are remote from an injection site of a neuromuscular blocking agent administered to the subject.

10. The system of claim 1, wherein the subject is experiencing neuromuscular paralysis caused by administration of a depolarizing or nondepolarizing agent, or a clinical condition mimicking administration of a depolarizing or nondepolarizing agent.

11. The system of claim 1, wherein the analysis of the muscle movement measurements embedded in the at least one signal includes identification of block-indicative markers of interest.

12. The system of claim 11, wherein the block-indicative markers are magnitude changes greater than a threshold.

13. The system of claim 12, wherein the magnitude changes are coincident, within a predetermined time period, of administration of a neuromuscular blocking agent.

14. The system of claim 1, wherein the degree of neuromuscular blockade is determined as a value on a scale, such as a numeric scale, percentage scale, or color-coded scale.

15. The system of claim 1, wherein the degree of neuromuscular blockade is indicated on a plot providing values for the subject over time.

16. The system of claim 1, wherein the muscle movement measurements include pre-block and post-block muscle movement measurements, and wherein the neuromuscular block analysis module is further configured to compare the pre-block muscle movement measurements to the post-block muscle movement measurements.

17. The system of claim 1, wherein the neuromuscular block analysis module is further configured to cause an average power associated with the muscle movement measurements in a frequency band of interest to be displayed on a user interface.

* * * * *